(12) United States Patent
Sliwa

(10) Patent No.: US 8,784,356 B2
(45) Date of Patent: Jul. 22, 2014

(54) ULTRASONIC ENDOVASCULAR CLEARING DEVICE

(75) Inventor: John W. Sliwa, Los Altos Hills, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1631 days.

(21) Appl. No.: 11/962,738

(22) Filed: Dec. 21, 2007

(65) Prior Publication Data

US 2009/0163940 A1    Jun. 25, 2009

(51) Int. Cl.
*A61B 17/20* (2006.01)

(52) U.S. Cl.
USPC .......................................................... 604/22

(58) Field of Classification Search
USPC .......................................................... 604/22
See application file for complete search history.

(56) References Cited

U.S. PATENT DOCUMENTS

| | | | |
|---|---|---|---|
| 6,551,337 B1 | 4/2003 | Rabiner et al. | |
| 6,660,013 B2 | 12/2003 | Rabiner et al. | |
| 6,685,657 B2 * | 2/2004 | Jones | 601/2 |
| 6,733,451 B2 * | 5/2004 | Rabiner et al. | 600/439 |
| 6,866,670 B2 | 3/2005 | Rabiner et al. | |
| 2003/0229331 A1 * | 12/2003 | Brisken et al. | 604/500 |
| 2004/0204729 A1 * | 10/2004 | Cimino | 606/169 |
| 2005/0043756 A1 * | 2/2005 | Lavelle et al. | 606/200 |
| 2005/0187514 A1 * | 8/2005 | Rabiner et al. | 604/22 |
| 2005/0215942 A1 * | 9/2005 | Abrahamson et al. | 604/22 |
| 2007/0112296 A1 * | 5/2007 | Wilson et al. | 604/22 |
| 2007/0161945 A1 * | 7/2007 | Nita et al. | 604/22 |
| 2007/0225619 A1 * | 9/2007 | Rabiner et al. | 601/2 |
| 2007/0270447 A1 * | 11/2007 | Hunter et al. | 514/274 |

OTHER PUBLICATIONS

International Search Report and Written Opinion for PCT/US2008/86558 mailed Feb. 10, 2009.
OmniSonics—Developing Medical Devices Utilizing OmniWave Technology, OmniSonics Medical Technologies, Inc., 2003.

* cited by examiner

*Primary Examiner* — Kevin C Sirmons
*Assistant Examiner* — Deanna K Hall
(74) *Attorney, Agent, or Firm* — Dykema Gossett PLLC

(57) ABSTRACT

An ultrasonic endovascular clearing device for use in a bodily lumen includes a powering handle configured to enclose one or more acoustic drivers, an acoustic amplifier and/or acoustic matching section including one or more amplifiers and/or matching elements and a driven wire. The acoustic drivers are configured to produce acoustic vibration in the ultrasonic frequency range. The amplifier/matching section matches and amplifies the acoustic vibration and drives the wire accordingly. The wire cleans due to one or both of a) its asymmetric shape being driven, b) its feature-enhanced surface being driven, whether on an asymmetric wire or not. The driving is pulsed or continuous, cavitating or noncavitating, and torsional or radial/lateral in its possible operational embodiments. A drug may be used by or delivered by the device and wire/tissue parameter sensing is optionally provided.

35 Claims, 3 Drawing Sheets

ULTRASONIC ENDOVASCULAR CLEARING DEVICE

BACKGROUND OF THE INVENTION a. Field of the Invention

The instant invention relates to an ultrasonic endovascular clearing device. In particular, the instant invention relates to an ultrasonic endovascular clearing device for clearing plaque, thrombosis and other blockages and/or restrictions in bodily lumens. Such lumens are typically natural lumens but may also include implanted lumens such as grafts and stents.

b. Background Art

It is known to employ various apparatus to clear fouled or blocked bodily lumens (e.g., blood vessels). Historically, conventional devices were incapable of the semi-invasive time efficient clearing of substantial lengths of lumen deposits in a reasonable time, if at all. For example, existing catheter-based devices perform their cleaning action only at their local tip position in the lumen. Such devices also have the propensity to cause lumen damage due to high balloon pressures (if they utilize balloons) and/or outright tip mechanical punctures of the lumen walls even if they do not utilize balloons. Restenosis is also a problem when such tissue insult is delivered.

A more recent approach in the art for endovascular clearing of blockages and other deposits involves an ultrasonic lateral-wave wire-based device. Such a device, in operation, involves the use of a small diameter titanium or titanium-alloy wire that is acoustically excited to transversely oscillate with multiple nodes and anti-nodes along its length. The oscillating wire is fed through fouled or blocked bodily lumens, with or without an assisting dissolution drug, to clean the lumen along its entire length simultaneously. Omnisonics of Wilmington, Mass. makes such a transverse oscillation wire system.

There are at least two issues with these wire-cleaning devices. The first and most clinically relevant is that it tends to be highly damped when routed around tight corners. This damping bleeds off most of the cleaning energy rendering the rest of the wire vibrationally ineffective. The lateral vibration mode is particularly subject to such damping.

The second issue is that such a device is subject to a certain amount of fatigue and that the large-displacement lateral or radial motions induce very high oscillatory wires stresses. Accordingly, such wires must be disposable (i.e., single or limited use). Although disposable wires are desirable for sanitary reasons, the fatigue described above increases the risk of a wire break during even a single use.

There is therefore a need to minimize or eliminate one or more of the problems set forth above.

BRIEF SUMMARY OF THE INVENTION

One advantage of the present invention is that the excitation approach taken is less prone to fatigue, thereby overcoming the fatigue problem described above. Another advantage of the present invention is that it is less subject to radial or lateral damping, overcoming the problems described above with excess damping in the art. It is desirable to be able to provide an ultrasonic clearing device for the removal or beneficial disruption of bodily lumen deposits including but not limited to plaques, thromboses, fat deposits and blood clots. Such deposits may also be those growing or depositing on the interior of implanted stents or grafts.

In one embodiment, a medical apparatus for use in a bodily lumen includes an acoustic driver and a flexible clearing member. The acoustic driver is configured to produce acoustic vibration in a torsional orientation. The flexible clearing member is coupled to the driver and is configured to be excited in accordance with the driving acoustic vibration. The clearing member is one selected from the group comprising a first wire type and a second wire type. Each wire type has a treating portion of its overall axial length configured to effect a clearing action in the bodily lumen. The first wire type has a longitudinal axis of rotation wherein at least the treating portion is asymmetrical with respect to the axis. When the first wire type is rotated about its axis, the radially-outermost portions of the wire along the treating portion effect the clearing action. The second wire type has surface features in the treating portion that are configured to effect the clearing action in the bodily lumen when rotated. This second wire type may be symmetrical or asymmetrical in cross-section with respect to the longitudinal axis.

In a preferred embodiment, the medical apparatus may further include an acoustic amplifying and/or matching section coupled to the acoustic driver and configured to acoustically amplify and/or acoustically impedance-match the acoustic driver's vibration to the flexible clearing wire member. The acoustic driver is configured to produce multi-wave acoustic vibration or discrete pulses at one predetermined operating frequency or pulse-period with the clearing member being torsionally oscillated or rotationally torqued in a rotational fashion substantially about its longitudinal axis and having a predetermined maximum operating amplitude. If pulsed rather than driven with a train of waves, the pulse(s) would likely have a chosen pulse waveform and maximum amplitude. The acoustic driver, the intermediate amplifying and/or matching section (if used), and the flexible clearing wire member are configured, with respect to each other, such that the rotational oscillation or pulsing of the wire at such operating frequency (or pulse-period) and amplitude is sufficient to cause cavitation, which effects accelerated clearing action mentioned above. In an alternate embodiment, another combination of frequency or pulse-period and/or amplitude is selected that is below a cavitation threshold, whereby the treating portion effects a mechanical (physical machining) clearing action with the radially-outermost portions of the wire. Such physical machining could be as by the erosive effects of the contacting wire and/or the acoustically excited fluid such as blood or delivered saline. It will be noted that a cavitationally driven wire will also deliver some amount of machining-based cleaning as well.

In a still further embodiment, the acoustic driver (and amplifying and/or matching section, if present) are configured to produce discrete acoustic wave pulses traveling down or along the flexible clearing member. Discrete means one or a few cycles or waveforms delivered at a time. These pulses, when temporally isolated and temporally spaced apart by an acoustic attenuation time-constant, will not produce standing waves. In particular, the acoustic driver is configured to produce temporally adjacent traveling wave pulses with at least an acoustic relaxation time in between each. The discrete pulses may be transverse (lateral) or torsional (rotational), or both. Note this pulsed transverse deflection versus torsional deflection embodiment of the invention.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
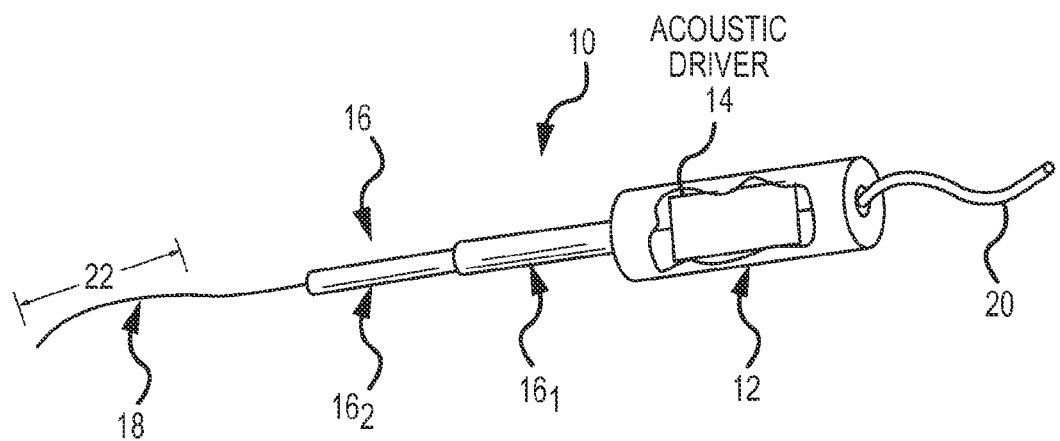
FIG. 1 is a diagrammatic view of an ultrasonic endovascular clearing apparatus according to the present invention.

Referring now to the drawings wherein like reference numerals are used to identify identical components in the various views, FIG. 1 is a simplified, perspective view of an ultrasonic endovascular clearing medical apparatus 10 for use in a bodily lumen. Apparatus 10 is characterized by an acoustically driven flexible clearing member (e.g., the treating wire 18 shown), operating in the ultrasonic frequency range and having a plurality of operating modes, including modes that employ acoustically-driven torsional waves. However, before proceeding to a detailed description of the present invention keyed to the drawings, a general overview of the various modes of operation will be set forth.

In a first acoustic mode of operation, apparatus 10 is configured to acoustically rotate, in a torsional orientation, a flexible clearing member at an operating frequency and amplitude (e.g., degrees of rotational deflection) selected so as to produce rotational displacement nodes and anti-nodes at least along its working length (i.e., a treating portion). Typically this will be done using a continuous or harmonic driving-waveform such as sine-wave. For contemplated treatments, tens, hundreds, thousands or millions of sine-waveforms will be delivered in a single continuous wave (CW) or multi-waveform episode. Because of the multiple waves, some degree of resonance attainment providing good conversion efficiency will be provided as will some accompanying degree of node and anti-node creation.

The flexible clearing member may be provided in the form of a first wire type that is asymmetrical (more below) or a second wire type that has certain topographical surface features, although the second wire need not necessarily by asymmetric. The first wire type has an elongated, flexible axis of rotation where at least a treating portion (i.e., a portion capable of delivering a clearing or cleaning treatment) is asymmetrical with respect to the wire longitudinal axis. The asymmetrical treating portion achieves a clearing effect by producing cavitation in or adjacent the bodily lumen while rotationally oscillating. Cavitation takes place because the fluid in or adjacent the bodily lumen is exposed to high negative pressures due to the rotating, non-round (i.e., asymmetrical) shape, which provides a piston like compressive and suction action at any given point on the treating portion. As is known, cavitation creates relatively intense shock waves, which are effective in this context to remove or disrupt even tough or hardened bodily-lumen deposits. The second wire type has topographical surface features that either project from the surface or extend into the surface and are configured to create cavitation when appropriately excited. The cleaning action of topographical wire-surface features can be attained both for round symmetrical wires and asymmetrical wires. On either type of wire the features themselves can contribute to abrasive or erosive non-cavitation machining and/or cavitation induction caused by their swept topographical shapes. Thus, cavitation can be caused by an un-featured rotating asymmetrical wire, by a moving topographical feature on any type of wire, and by a topographically featured asymmetrical wire. The latter cavitation possibly being caused for the two different reasons, presuming the wire driving amplitude is high enough.

In a second acoustic mode of operation, the flexible clearing member (i.e., either the first asymmetric wire type or the second symmetric wire type) is also acoustically rotated in a torsional orientation, either in a continuous-wave or multi-waveform fashion, which is the same as in the first acoustic mode, but below a cavitation threshold. As a result, the axially-extending clearing (or cleaning) action provided along the treating portion occurs in a purely mechanical manner (i.e., physical erosive machining by the moving wire or by its adjacent moving fluid). For example, where the flexible clearing member is square in cross-section, it would perform micro-abrasive cleaning at its corners along its treating portion in a torsional mode. This second mode of operation, like the first, will have nodes and anti-nodes presuming continuous or many-cycle driving. Again, one may also combine an asymmetrical wire with surface-features and operate it below or above a cavitation threshold.

In a third acoustic mode of operation, the apparatus is configured to produce substantially discrete acoustic wave pulses that individually travel down the flexible clearing member. The wave pulses may exhibit either lateral (transverse) displacement and/or torsional displacement. Delivering both types simultaneously or in an interleaved fashion is also possible. Unlike the standing-waves associated with the first and second modes of operation, which can involve both forward-going and backward-going waves constructively interfering to produce nodes and anti-nodes, this pulsed third mode of operation principally employs forward going waves (i.e., originating with and moving away from the driving transducer). Typically, each pulse is discontinued in time long enough to allow for rotational (for torsional waves) and/or translational (for lateral waves) oscillatory attenuation to occur (i.e., an acoustic relaxation time) before another driving pulse (if any) is applied. In this manner, full-resonance is not only avoided but little if any resonance in any amount is achieved. At the same time, little or no standing periodic nodes and anti-nodes are formed. This mode can therefore uniformly treat a length of the bodily lumen that surrounds the treating portion with no required lengthwise wire dragging or node/anti-node scanning (as by varying frequency) by the user. Eliminating the need to drag the wire back and forth reduces the risk of doing any kind of puncture or other damage to the bodily lumen. Such single or short pulses can be at driver power levels above those used for continuous (resonant) operation to attain equivalent cleaning rates. Again, such a wire may or may not have surface features and may or may not operate above a cavitation threshold.

With this general introduction to the modes of operation, and with continued reference to FIG. 1, apparatus 10 comprises a housing 12 including an acoustic driver 14, and an optional, but preferable, acoustic amplifying and matching section 16 including one or more individual acoustic amplifiers and/or acoustic matching elements, such as a first amplifier/matcher 16₁ and a second amplifier/matcher 16₂. FIG. 1 further shows a flexible, clearing member such as an asymmetrical driven wire 18 or a surface-feature laden wire 34 (FIG. 4) that is acoustically coupled to the driver 14 and is configured to be excited in accordance with such acoustic vibrations. As shown, wire 18 has a main longitudinal axis designated "A" in the Figures (best shown in FIG. 2). The wire 18 also has a treating portion 22 of its overall axial length (i.e., that portion which is configured to effect the beneficial erosive clearing and/or cleaning treatment in the bodily lumen). Some or all of treating portion 22 may contain the taught symmetrical/asymmetrical shapes and/or the topographical surface features.

Housing 12 is configured in size, shape and material to provide a suitable slippage-resistant gripping handle for manual manipulation of apparatus 10 by a user or endovascular practitioner (neither user nor practitioner shown). Housing 12 is preferably configured for multi-use operation (i.e., is non-disposable) and is therefore preferably configured to allow repeated cleaning or sterilizing. A non-disposable housing 12 is an attractive strategy if the wire 18 is itself exchangeable or disposable. In an alternate embodiment, housing 12 and wire 18 may be provided in a disposable package not intended to be separated by the user and likely designed for one or a limited number of uses. With a disposable wire and non-disposable housing scheme one could use a disposable sheath over the handle portion such that between procedures handle 12 only needs a wet sterilant exposure or hydrogen peroxide-based cleaning.

The housing 12 may be further configured to include one or more other features such as a power switch (i.e., on/off switch), a power adjusting control, a mode-selection control, a wire-integrity indicator, a power on/off indicator or even a mechanism to apply a net rotation or translation to the wire separate from the above inventive driving cleaning movements (none of these shown).

Housing 12 is still further configured to enclose one or more acoustic drivers 14 (one driver being shown in FIG. 1). The driver 14 comprises at least one transducer of any suitable type, such as a piezo-transducer, an electrostrictive transducer, an electromagnetic transducer, a magnetostrictive transducer or even a pneumatically or fluidically driven vibrator. Several transducer options exist and the above are exemplary only and not limiting in nature; however, piezo-transducers are preferred because of their flexibility in the many continuous and pulsed waveforms that can be applied to them and the fact that they can provide feedback. The driver 14 may also include electrical circuitry, electrical matching circuitry and a step-up voltage transformer and high-voltage switches. Accordingly, "driver" as used herein refers to the structure or structures corresponding to the collective transducer function, including its powering or firing circuits. Electrical power may be provided to the internal circuitry in housing 12 (including for the selective energization of driver 14) by a conventional power cord 20. The power cord 20 may also be configured to be replaceably detached from the housing 12. While the device is shown including the power cord 20, it should be appreciated that other power sources may be used in lieu of line power, including but not limited to the following power sources: battery, fuel cell, super-capacitor or other internal or functionally-integrated stored energy sources. In an embodiment where apparatus 10 is battery-powered, the housing 12 may be optionally configured to internally house such batteries. In a further alternate embodiment, such batteries may be rechargeable using a separate or in-line recharger sold with the apparatus.

Housing 12 is also preferably configured to be water (or other fluid) ingress-resistant so as to improve the functionality and use/patient safety of apparatus 10. Alternatively, as mentioned above, apparatus 10 may be used with a water or liquid resistant (or water proof) sheath, cover, membrane or bag overlying or enveloping at least the housing 12. Such a disposable sheath, bag, membrane or cover may be advisable simply for sterility reasons even if the handle has been cleaned or disinfected between patients.

Apparatus 10 will likely include a control box or console (not shown). Such a box or console may be configured to have an informational and/or control GUI (graphical user interface) and a display capability for displaying at least basic information, such as the operation mode, power status and perhaps patient information. Such a box may be console-based or portable and may have wired or wireless network interface functionality. In still further embodiments, some of the above-described electronic circuitry, such as power supplies, switches or matching networks, may be provided in such a box rather than in the housing 12 in order to reduce the size, weight and cost of the handheld device portion regardless of whether the handle 12 is disposable or not.

Figures 2A, 2B:
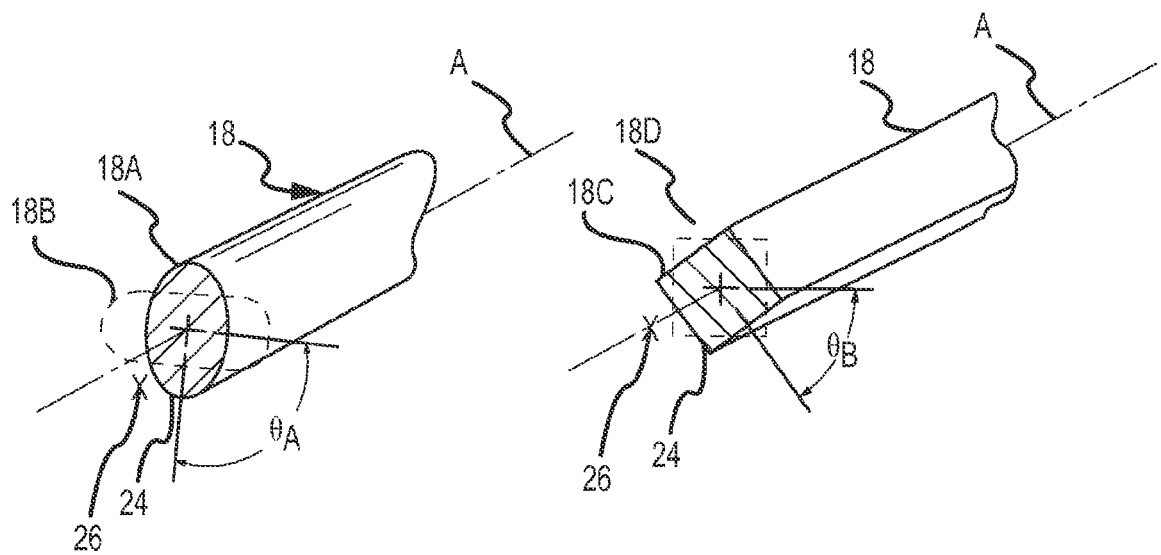
FIG. 2A is a perspective view showing an embodiment of a flexible wire portion of the apparatus of FIG. 1.
FIG. 2B is a perspective view showing an alternate embodiment of the flexible wire portion of the apparatus of FIG. 1.
Figures 4, 5, 6:
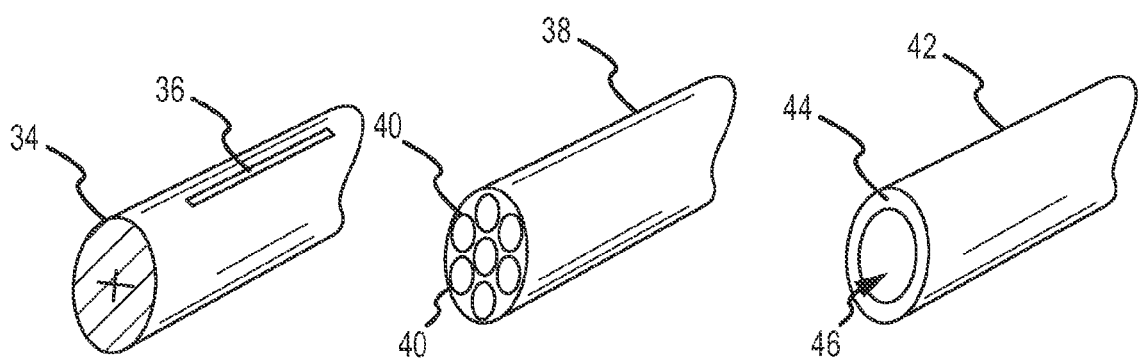
FIGS. 4-6 are perspective views showing still further, alternate embodiments of the wire portion of FIG. 1.

Acoustic driver 14 (collectively if multiple drivers 14 are present) is configured to produce acoustic vibration in at least one preselected orientation relative to axis "A" of FIGS. 2A-2B, such as torsional or transverse, consistent with the selected mode of operation. As described above, there are three basic acoustic modes of operation contemplated by the present invention: (1) a continuously acoustically driven, torsional rotation mode of operation wherein the clearing action is substantially produced primarily via cavitation; (2) a continuously acoustically driven, torsional rotation mode of operation wherein the clearing action is produced primarily mechanically via wire/fluid physical machining by the radially-asymmetric shape of the wire; and (3) an acoustically driven, torsional or transverse traveling wave pulse mode of operation, wherein adjacent traveling wave pulses are separated by approximately an acoustic relaxation time or longer (to avoid fully-developed standing waves) wherein the clearing/cleaning action is accomplished by cavitation and/or by mechanical/fluid action. Acoustic driver 14 may comprise conventional apparatus known to those of ordinary skill in the art, such as torsional piezotube transducers. It should be understood that "mechanical" lumen cleaning may include cleaning action not only caused by the direct contact with the wire but by the fluidic influence of energetic or microscopically violent fluid flow induced by the nearby moving wire as well. Both of these produce erosive and disruptive effects. Note again that a symmetrical or asymmetrical wire might have surface-features (asymmetrical as depicted in FIG. 4) and operate above or below a cavitation threshold.

With continued reference to FIG. 1, any acoustic amplifiers/matchers 16₁ and 16₂ which are utilized are configured to amplify the oscillatory motions of driver 14 and/or to acoustically impedance-match the transducer driver 14 to a much smaller wire (e.g., wire 18) as these have different acoustic impedances as seen by the propagating waves. Acousticians will recognize that the use of acoustic amplifiers and/or acoustic matching components are preferred to provide for energetically efficient operation. Electrical matching (as opposed to acoustic matching) circuitry may also be provided as is again typically preferred, particularly if the driving electronics are several feet away from the transducer or if the connecting cable 20 is impedance-mismatched to the transducer. Amplifying and matching sections 16 are further configured to drive wire 18 with the amplified, acoustic vibration (1) torsionally in a pulsed or continuous manner and/or (2)

laterally in a pulsed manner. As illustrated, amplifier/matcher $16_1$ and $16_2$ comprise progressively decreasing diameter (or tapered, not shown) sections, as would be understood by one of ordinary skill in the acoustics art. The particulars of each amplifier/matcher, including the number of sections and their respective diameters, lengths, etc., may be varied to accommodate the broad range of operating frequencies and amplitudes contemplated by the present invention. In addition, the acoustic amplifiers and/or acoustic matching elements, or one of them (if present), are configured so as to accommodate manufacturing tolerances associated with any particular version of wire 18 that is used. In alternate embodiments, the apparatus may include various combinations of wires and amplifying/matching sections, either configured to be connectable (e.g., by the user or practitioner) or as prejoined combinations.

An alternate embodiment of apparatus 10 may be formed without the acoustic amplifier and/or matching elements, however, this is less preferred because that approach typically requires running the transducer-driver or transducer portion of the driver very hard to overcome poor impedance matching, low efficiency, and/or to provide sufficiently large oscillatory displacements so as to incur an increased risk of driver failure.

As described above, the flexible clearing member, namely, the wire 18, has a treating portion 22 that may or may not be the same shape or design as the rest of wire 18. In other words, wire portion 22, for example, might have surface topographical features and/or an asymmetrical nature whereas the remainder of wire 18 might be the same or might instead be round, symmetrical or other un-featured shapes. The treating portion 22 may be but need not be a sub-section of its overall axial length.

For the first and second modes of operation, the treating portion 22 of the wire 18 is asymmetrical with respect to the flexible, wire longitudinal axis "A". In this regard, an asymmetrical wire is defined as a wire whose cross-section, taken normal to the elongated flexible axis and, at least in some of the treating portion 22, has a radius that is variable as a function of rotational orientation or angle. Note that this definition would include, for example, a bow-tie shaped wire section despite its having a self-mirroring characteristic. The term "radius", for a noncircular cross-section, may refer to a polar vector or vector set which defines the wire perimeter (and thereby the section) relative to a reference point such as relative to a reference point inside the perimeter, such as a center of mass. In view of this definition, any wire which is not round (i.e., has a varying polar radius) is asymmetric. Moreover, the asymmetrical cross-sectional shape along the treating portion 22 of the wire 18 may be constant. Alternatively, the wire can be configured so that the asymmetry varies as a function of axial position within and along the treating portion 22. Such an asymmetrical shape could be, for example, oval, elliptical, square, rectangular or prismatic in nature or a combination of those shapes. As the asymmetric wire oscillates, adjacent tissue will experience a cyclic stress. Further, fluid displaced at the radial corners or edges of such wires 18 along treating portion 22 will create fluid shock waves, if not cavitation, under suitably high enough driving power levels for continuous wave or pulsed wave operation. Alternatively, wire 18, for the third mode of operation, need not be asymmetric, as described above.

As to a preferred construction, wire 18 may be a solid (single) strand and most preferably comprise titanium metal or one of its alloys, inasmuch as titanium (or its alloys) has desirable acoustic properties and features medical compatibility. However, the construction material of wire 18 is not limited to titanium or titanium alloys. In alternate embodiments, for example, wire 18 may utilize, generally, known body-compatible metal material, electrically-conductive material, optically-transmissive material, and more specifically, stainless steel material, wire comprising other metal alloys such as that commercially available under the trade designation NITINOL®, particularly super-elastic NITINOL® wires, and glass or ceramic material. NITINOL® is a family of inter-metallic materials that contain nearly equal mixture of nickel (55 wt. %) and titanium, and is available, for example, from Nitinol Devices and Components (NDC), Wayzata, Minn., USA. In addition, wire 18 may comprise low acoustic loss material. Low acoustic loss means acoustic losses that are preferably less than about 5 dB/cm/MHz, more preferably less than about 2 dB/cm/MHz, and most preferably less than about 1 dB/cm/MHz. It should be recognized that in the pulsed modes of operation there is less concern for metal fatigue and optimal acoustic impedance matching than for the continuous-wave modes of operation. Accordingly, the pulsed modes of operation allow for a broader range of wire types and materials to be used. Wire 18 might even be a hollow tube or a multi-strand micro-cable.

Additionally, wire 18 and/or wire portion 22 may inherently be either straight (e.g., as would be observed as it lays on a table or the like) or non-straight (e.g., subjected to various pre-stressing to achieve a biased shape) or have a slight screw-type shape along its length. It should be appreciated that this global shaping is independent of the cross-section shape in at least some embodiments. It should be understood that wires consistent with the present invention may be extruded or drawn in a modest-cost manner into desired lengths and shapes. Additionally, such wires may be laser-machined or electro-discharge machined at a somewhat higher cost. Further, additive techniques such as electroforming of laser deposition could additively fuse material or topographical shapes to an otherwise round (or even asymmetrical wire. Wires can even be ground using grinding arrangements. Finally, it should be understood that "wire" merely refers to a relatively long, slender, flexible member that is configured to be fed into a lumen. It should be understood that the term wire is not limited to the conventional and perhaps common meaning of a drawn metallic wire, but rather, is broader and encompasses nonmetallic materials formed through other processes (i.e., not only being drawn). Thus the "wire" 18 might also comprise an optical conduit or fiber wherein it performs both the cleaning function and an additional optical therapeutic diagnostic or sensing function.

In a preferred embodiment, wire 18 is disposable and is configured to be mounted in or coupled to a non-disposable handle (e.g., as may be defined by the housing 12), although as described above, the housing/handle and wire may be an integrated combination not intended to be separated by the user. The wire 18 may be provided, for a given desired cross-section, in a number of lengths. Various model wires with different flexibilities and cross-sectional shapes may be provided to address a variety of patients and deposits or blockage types. The wire 18 may also be configured so as to allow it to be cut or trimmed on-site to a desired length or may be strung through the transducer itself (not shown) such that its treating portion 22 can be adjusted without having to trim or cut the wire 18.

FIGS. 2A-2B show two exemplary embodiments of wire 18. In FIG. 2A, an oval or elliptical-shaped wire 18 is shown. Oval wire 18 is shown in an undisturbed, first position 18A and in a torsionally deflected second position 18B (shown in dashed-line format). Also note that the rotation is preferably in a reciprocating (back and forth) fashion for continuous wave operation and non-reciprocating (not continuously reciprocating) for pulsed operation. While the illustrated amount of the deflection in FIG. 2A, designated as $\theta_A$ degrees, is exaggerated as being approximately 90° for ease of illustration, the actual maximum angular excursion $\theta_A$ may typically be substantially less than 90 degrees or in some cases even more than 90 degrees. To achieve the cavitation effect, acoustic driver 14 is configured to produce acoustic vibration at a predetermined operating frequency within an ultrasonic frequency range, preferably in the 20-150 kHz range for typical lumen-compatible wires. In FIG. 2A, tissue, blood or fluid point or region 26 will cavitate if swept rapidly as radially-outermost portions 24 of wire 18 (i.e., the asymmetrical oval shape) withdraws from that space upon each cycle of torsional displacement 18A/18B. Variations that employ predisposed cavitation nuclei to facilitate the occurrence of cavitation, now known or hereafter developed, are included within the scope of the present invention. For example, certain cavitation nuclei such as the known gas-filled micro-bubbles substantially reduce the energy threshold required for cavitation. This variation can also improve wire fatigue-resistance due to the decreased deposited energy. Any of the wires may be utilized in combination with a flushing/cooling agent such as saline as, for example, delivered by a wire-containing catheter lumen.

FIG. 2B is similar to FIG. 2A, and shows wire 18 having a square (or rectangular) shaped radial cross-section. FIG. 2B shows a first, undisturbed position 18C and a second, torsionally deflected position 18D (dashed-line format). While the illustrated amount of the deflection in FIG. 2B, designated as $\theta_B$ degrees, is exaggerated as being approximately 45° for ease of illustration, the actual maximum angular excursion $\theta_B$ may be typically substantially less than 45° or even more than 45° in some cases. Again, tissue, blood or fluid point or region 26 will cavitate when wire 18 is rotated very rapidly. Again, maximum deflections may be less than this while still achieving useful torsional continuous wave or pulsed (cavitation or non-cavitation) treatments. Additionally, as described above, the third (pulsed) mode of operation provided for translational (as well as torsional) pulsed displacements, and in this regard, such translational displacements may be below or above a predetermined threshold or limit for cavitation.

Acoustic driver 14 is typically configured such that the driving frequency or frequencies will be fixed and chosen to favorably excite an approximate desired number of rotational nodes and anti-nodes. Additionally, for any particular configuration (including for any particular operating frequency), the wire 18 will have a maximum (e.g., safe) operating amplitude. It should be understood that during operation, the driver 14 will be controlled so that the rotating wire will have at least one operating amplitude that is no greater than the predetermined maximum amplitude described above. In alternate embodiments, however, acoustic driver 14 is configured to provide broader-band driving and variable frequency driving of the wire as well as driving the wire at its self-detected optimal driving condition for that particular wire and/or for the wire-loading at a moment of use. Thus a likely scenario is that the wire 18 is designed for a nominal driving frequency or pulse-period and onboard tuning circuitry identifies the optimal driving frequency which might be somewhat different due to tolerance and/or bodily loading or practitioner-manipulation factors. In addition, the acoustic driver 14, as with the amplifying/matching elements (if present), is configured so as to accommodate manufacturing tolerances associated with any particular version of wire 18 that is used.

In general, continuous-wave operation, such as at a fixed frequency, will produce standing or slowly (axially) moving nodes and anti-nodes of maximal resonant rotational displacement. These standing or slowly moving nodes and anti-nodes will produce the maximal rotational or torsional cavitation assuming the driving power is high enough and produce the maximal rotational displacement without cavitation if the power is below the cavitation threshold.

For both the first and second modes of operation, one could "scan" the nodes and anti-nodes lengthwise relative to a surrounding lumen by one or both of varying the driving frequency or pushing and pulling the cleaning wire a distance about equal to the nodal spacing. In this regard, the acoustic driver 14 is configured to vary (i.e., either by virtue of pre-programming or by user control) the operating frequency of the acoustic vibration over a predefined time period (i.e., if pursuant to pre-programming) or a controlled time period (i.e., if user controlled) to effect scanning of the nodes and anti-nodes axially along at least the treating portion.

Additionally, the torsional mode of operation is capable of treating the entire circumference of the lumen at a given axial position. This is true for either the first wire type (asymmetrical) or the second wire type (surface features). Thus, torsional operation is beneficial for uniformity as well. In the typical case where the torsional wire is smaller in cross-sectional size than its surrounding lumen, one could assure cleaning of all surrounding lumen walls as by (a) twisting the driven wire to vary its radial contacts and/or (b) providing the wire with a mild helical shape along its length such that it self-biases against the lumen walls.

It cannot be overemphasized that the present invention, in the various modes of operation, achieves cleaning therapy through (1) cavitation-induced erosion and breakup of plaque, thrombosis or deposits and/or (2) mechanical/physical/fluidic abrasion and erosion of plaque, thrombosis or deposits as by the mechanical action of an edge or other radially-outermost portion of wire 18 or by fluidic pressure-wave or shock-wave erosion. Either or both mechanisms can be engaged in continuous, standing wave fashion or in a pulsed fashion. Additionally, in an alternate embodiment, apparatus 10 may be configured to operate to employ cavitation and physical-machining, either sequentially or simultaneously.

Figure 3A:
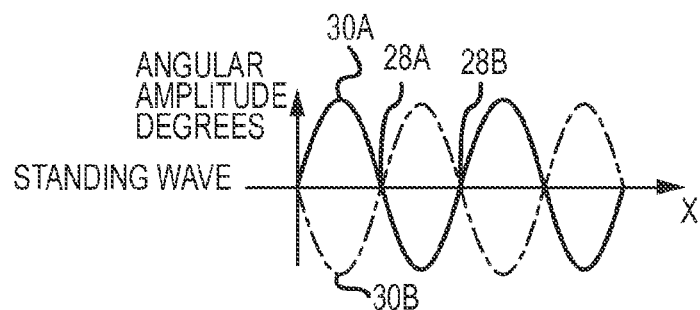
FIG. 3A is a displacement-versus-axial position diagram showing a standing wave with nodes and anti-nodes from a torsional vibration of the wire of FIG. 1.

FIG. 3A is a torsional displacement-versus-axial position ("X") diagram depicting a continuous wave (CW) standing waveform existing in wire 18 upon continuous excitation by acoustic driver 14 and any amplifying/matching section 16. The torsional displacement is shown in exemplary fashion in angular degrees at various axial positions along the length X of wire 18. Additionally, the standing wave of FIG. 3A corresponds generally to the first torsional cavitation and torsional, physical machining modes of operation described above (i.e., first and second modes of operation).

FIG. 3A depicts two complete sinusoidal cycles of a continuous wave (CW) excitation signal likely comprising many more than two driving cycles. Accordingly, four nodes of the type 28A and 28B, with essentially zero displacement, and eight anti-nodes of the type 30A and 30B, with maximal displacement are shown in exemplary fashion. In FIG. 3A, wire position 30A and the second torsional extreme wire position 30B is offset 180 degrees in temporal-phase from position 30A. It should be understood that a plurality of predefined combinations of operating frequency and operating displacement (amplitude) will be operative to establish the standing wave in FIG. 3A, in view of the capabilities and characteristics of acoustic driver 14, transformer 16 and the selection of wire 18. In this regard, in a preferred embodiment, acoustic driver 14 may preferably be configured to include auto-tuning capability (i.e., an auto-tuning driver circuit, which may include an electrical impedance matching component).

Figure 3B:
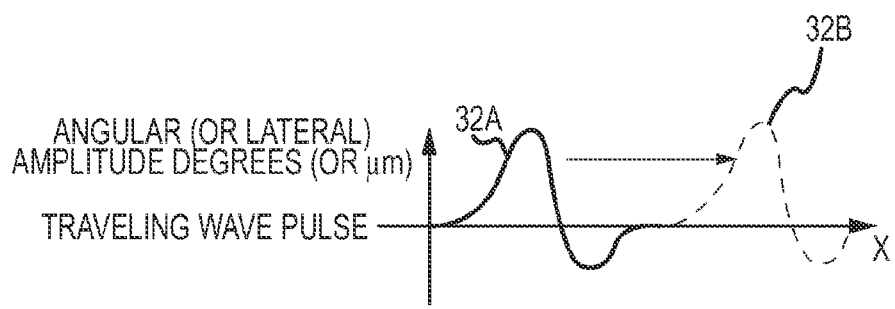
FIG. 3B is a displacement-versus-axial position diagram showing a single acoustic wave pulse traveling on the wire of FIG. 1, according to an alternate embodiment of the invention.

FIG. 3B is a torsional (or lateral) displacement-versus-axial position ("X") diagram depicting a discrete rightward-moving or traveling acoustic wave pulse 32A, as distinguished from a standing wave as shown in FIG. 3A. The wave pulse 32A of FIG. 3B corresponds to the third mode (traveling discrete-wave pulse) of operation described above. The same discrete pulse 32A is depicted as propagating at the wires sound velocity from a first, left position to a second, right position 32B (away from first position 32A) along the X-axis or axial length of wire 18. A torsional pulse would have an amplitude measured in degrees whereas a lateral pulse would have an amplitude measured in microns, for example. It should be understood that wave pulse 32A need not be symmetrical in shape (amplitude versus time), i.e., the shape can and typically will be irregular as depicted in FIG. 3B. The shape may be unipolar or bipolar in nature (bipolar or positive/negative shown). This pulsed waveform may be, for example, torsional, lateral or both. As alluded to above, the acoustic driver 14 is configured to produce acoustic vibration so that adjacent wave pulses are separated by about an acoustic relaxation time or longer (e.g., 1 milliseconds-long delays). This degree of separation ensures that no significant standing wave is established. The wave pulse 32A can conform to a lateral (transverse) generated wave pulse and/or it can conform to a torsionally generated wave pulse, so long as adjacent instances of the wave pulse type are separated by their respective acoustic relaxation or attenuation time.

Discrete pulsed wave operation has some different inherent advantages than continuous or CW operation. "Discrete-pulsed" means any driving scheme that is not temporally continuous in energy application, particularly one that is not harmonically, temporally continuous as is a continuous sine wave for example. "Discrete-pulsed" driving, as described, will typically avoid standing waves in the wire for that particular driving mode in question. Note that one could even have continuous standing-wave torsional mode operating in cooperation with a separate pulsed transverse mode.

Discrete pulsing operation allows for waveforms to travel along the wire in a manner such that they do not have standing nodes and anti-nodes because there is not enough energization time for resonance to develop and/or because the pulses have purposely varied periodicity and therefore no particular common resonance frequency or harmonic frequency.

Discrete pulsing results in delivery of the same amplitude everywhere axially over time (accounting for some natural attenuation versus length) along the wire such that treatment is axially uniform as opposed to axially periodic due to a standing node/anti-node resonant condition. Although one gives up the maximally energy-efficient high-amplitude of the resonance condition, one can drive the wire harder for discrete pulses making up for some or all of that loss. Also note that all portions of the axial wire see the same stress history during deflection unlike the standing-wave condition—again ignoring some attenuation or damping by lumen-loading along the length. This means that discrete wave methods have more leeway with respect to avoiding wire fatigue. Thus, delivering a series of discrete separated yet rapid pulses one can treat more uniformly in the axial direction without requiring wire dragging. Secondly, one can utilize the pulsing scheme for other purposes, such as performing pulse-echo assessment of the wire's integrity or of the wire's loading state against tissue or blood. Such pulsing can also be useful for feeding the wire into and out of the lumen. Thirdly, because cavitation typically takes multiple connected cycles to occur, this approach is a way to deliver high non-cavitating energy. Fourth, the wire will heat less in the pulsed state. Finally, pulsing can be done in a manner wherein, for transverse lateral pulsing, the lateral displacements are variable in direction (away from the axis) from pulse to pulse. This directional variation can further assure equivalent exposure of tissue contact regions regardless of orientation.

The use of sensing or probing pulses to assess the wire's health or tissue coupling state has been described herein. The acoustic practitioner will realize that such an approach would likely comprise a pulse-echo approach and that such pulses could be therapeutic torsional or transverse pulses or could be non-therapeutic longitudinal pulses not mentioned until this point.

As described above, the driver(s) 14 may be arranged to drive the wire 18 in one or both of a torsional or lateral displacement direction for therapy application. In this regard, the driver 14 may be configured to simultaneously or sequentially combine the two displacement types and in such an embodiment it should be understood that the respective relaxation times for each of those wave types may be different. The driver 14 may be configured when driving both wave types, to produce such wave types in an overlapped, interleaved, sequential or simultaneous manner such as wherein their respective relaxation times are individually applied only to that respective wave type. One of ordinary skill will recognize that if one has simultaneous-going torsional and lateral waves that their respective attenuation decay times (acoustic relaxation times) may be acoustically modified somewhat from the case wherein the waves operate separately.

FIG. 4 shows an alternate embodiment of the clearing wire, designated by reference numeral 34, including one or more wire surface feature(s) 36 configured to provide the desired cleaning function, as by physical micromachining of the wire/fluid as induced by the surface feature and/or as by cavitation induced by the surface feature. The one or more wire surface feature(s) 36 may be (1) at least one positive surface feature extending from or beyond an outer surface of the wire; and/or (2) at least one negative surface feature extending from or into the surface of the wire; and/or (3) one or more texture or topography provision, whether temporary or permanent and regardless of whether a different material other than the underlying wire material is involved.

The positive surface features may include at least one additive feature selected from the group comprising an electro-formed material, an electro-deposited material, an electro-plated material, an adhered material, a bonded material and a texturing or roughening of the wire surface during wire formation such as by drawing or extrusion formed onto or from the second wire surface. Plasma or flame/torch deposition of surface features might also be practiced.

The negative surface features may include at least one subtractive feature selected from the group comprising an etched feature including a laser-etched machined feature, an electro-discharge machined feature and a texturing or roughening of the surface during wire formation formed into or from the second wire surface. Note that even if such features are distributed uniformly about the wire radius and even if the wire is generally round (oval shape shown in FIGS. 4-6), the features can still cause tissue machining/erosion and/or cleaning. These features might be asymmetrically disposed angularly on the wire surface but may also be uniformly, circumferentially distributed. Typically, but not necessarily, the topographic height variations of surface features will be smaller than the variation of radii in the above asymmetric wires. Surface features thus may reside on asymmetric wires or on round symmetric wires. As in the asymmetric wire embodiment, these features can produce cavitation (or not) depending on the driven power level. Such features can provide erosive fluidic and/or direct wire-contacting cleaning effects.

In the illustrated embodiment, wire 34 may have, for example, laser-machined surface features, such as a depicted trench or slot feature 36, formed thereon configured to enhance cavitation and/or physical or fluidic abrasion or erosion. Similarly, such surface features may extend radially-outwardly from the wire surface. This can be done in a way where the machining or additive processing is automated and wherein the features do not introduce unacceptable stress concentrations. For example, a slight electro-polishing after subtractive laser-machined feature-definition can be employed for this purpose. Note that a wire, even a symmetric round wire, with such a surface-defined feature is operative in the present invention. Also note that such surface features may be additive in nature, as in an applied feature which is additively attached, as opposed to subtractive in nature, as by removal through being etched or machined. It should be understood that such additive or subtractive surface features may reside on asymmetric wires or on round symmetric wires.

In view of the foregoing, it should be apparent that the wire 18 can be effective in cleaning lumens or blockages due to either its asymmetry (if any) and/or due to its surface features (if any).

FIG. 5 shows a further clearing wire embodiment designated clearing wire 38. The wire 38 comprises a plurality of individual sub-strands 40, each of which may be smaller than the size of the overall clearing wire 38 itself and each sub-strand may be solid. The plurality of strands 40 may be solidly packed or wound as in a cable. An overcoating and/or impregnating bundle potting may be provided as shown. The depicted wire bundle has 7 strands and an impregnating overcoating. Such impregnations, over-coatings and/or bundle potting material can carry or comprise drugs which are released in the lumen. They may also comprise lubricants to aid in wire insertion after which they may substantially dissolve if desired. Note that a multistrand wire is highly unlikely to fracture instantaneously.

FIG. 6 shows a still further clearing wire embodiment designated hollow wire 42, which has a thin-wall structure 44 defining a central cavity 46, which itself might be used as a fluid lumen or a lumen for an electrical lead or fiber-optic member. The central cavity 46 when used as a lumen may be used to communicate either a fluid pressure or a pneumatic pressure. Alternatively, central cavity 46 when used as a lumen may be used to communicate a fluid flow or a pneumatic flow, where such flow may be a coolant liquid or a drug-delivery liquid, and may be in an inward (toward the handle) or outward (away from the handle) direction. Thus, the "core" or internal region of the wire may be solid, liquid or gaseous. A hollow-core wire 42 may comprise commercially available components, such as a length of NITINOL® super-elastic micro-tubing, available from Nitinol Devices and Components (NDC), Wayzata, Minn., USA.

In any of the inventive embodiments one might elect to utilize an electrically conductive wire (or one which can be rendered conductive as by a thin-film deposition) to conduct an electrical current or communicate a voltage potential such as to a sensor mounted on the wire tip (not shown).

Additional embodiments of the clearing wire may comprise an optical fiber core or being entirely comprised of an optical fiber possibly with an optical over cladding. Alternatively, the clearing member may include a plurality of optical fibers, and may be either coated and/or impregnated with a drug or medicament to be delivered. Still further embodiments of the clearing wire may comprise a solid or hollow or multilayer wire, which may include an infused, over-coated or internally-residing drug or medicament that is configured to be delivered to the lumens with or without the help of the ultrasonic energy. Note again that the potted infiltrated multistrand wire bundle of FIG. 5 could incorporate outdiffusing drugs for example.

Figure 7:
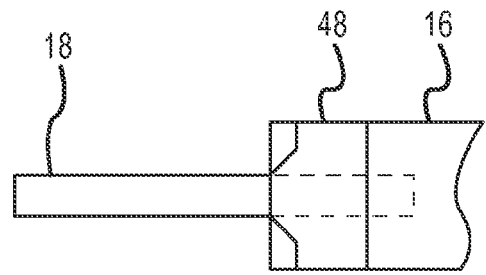
FIG. 7 is a plan view showing a mechanism for easily removably attaching the wire of FIG. 1.

FIG. 7 is a partial, fragmentary side view showing a mechanism, such as a pin vise 48, for easily removably attaching wire 18 to amplifying/matching section 16. This mechanism 48 permits removal and disposal of the wire 18 after one use (i.e., the wire being exchangeable for another wire for the next use) or removal and sanitization of the wire 18 for reuse (i.e., if the wire is not to be disposable). This facility also enables wire 18 to be provided in a kit of multiple lengths, sectional shapes or sizes or wire/catheter combinations that can be selected by the user of apparatus 10. Pin vise 48 may comprise conventional components known in the art. Pin vise 48 may be adapted to clamp round or nonround asymmetrical wires. An overly long wire 18 might be pin-clamped at a useful length and the excess either hung out the handle-end or cut off by the practitioner. As with the acoustic driver 14 and the amplifying/matching elements (if present), the pin vise 48, if used, may be configured to accommodate manufacturing tolerances of any particular version of wire 18 that is used.

Figure 8:
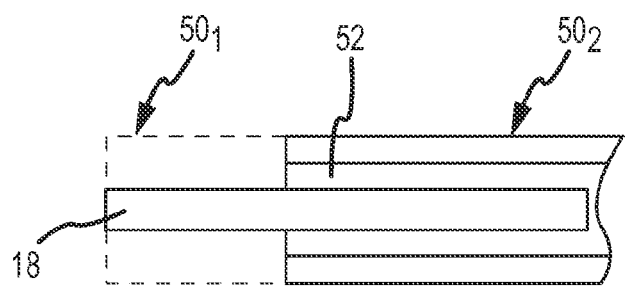
FIG. 8 is a partial, fragmentary plan view of the wire of FIG. 1 in combination with a catheter.

FIG. 8 is a partial, fragmentary side view of a wire/catheter combination. In FIG. 8, a catheter $50_1$ (shown in dashed-line format) is shown in a first position in which it is disposed radially outwardly of or containing-of the treating portion 22 of wire 18 to thereby enclose the wire 18, particularly at least a subpart of the treating portion 22. This position may be used for insertion into the bodily lumen. The catheter is further configured to assume a second position $50_2$ (shown in solid line) axially offset and away from the first position $50_1$ wherein the at least subpart of the treating portion 22 is exposed for use in treatment. The catheter $50_2$ may include one or more lumens (e.g., one lumen 52 is shown) configured for at least one operation selected from the group comprising (1) delivering or guiding the flexible clearing member to a treating location; (2) delivering a desired drug or an imaging-contrast or cavitation agent, such as a deposit dissolution drug, to a location proximate or near the treating portion 22 of wire 18 (e.g., in cooperation with a clearing/cleaning therapy); (3) delivering flushing or aspirated liquids; (4) removing flushing or aspirated liquids; and (5) inflating or draining a balloon portion of a balloon-based device (e.g., to inflate the balloon portion). The catheter or sleeve 50 may be arranged to be slippery on the inside to reduce friction between the wire 18 and the catheter or sleeve 50 either during insertion, during treatment or both. In other words, the wire and catheter/sleeve may be configured to allow the user (or practitioner) to choose to operate the wire for treatment with only its treating portion 22 (or sub-portion thereof) exposed to the lumen. Thus, to reduce losses (due to vibration) from the wire 18 to its surrounding catheter or sleeve 50, the apparatus may be configured to include axially-extending (or radially-extending, which is not shown) surface topography or isolated bearing surfaces between the wire and the sleeve to reduce that friction. Sleeve 50 may also be delivered or preconditioned with a wet or dry lubricant. Sleeve 50 is configured to protect the lumen from damage or abrasion from the wire entry point into the body up to where the treating portion 22 of the wire becomes exposed to the lumen. It can also serve to minimize acoustic losses of energy before it arrives at wire treatment region 22.

Although not preferred, included in the inventive scope of the invention is an apparatus 10 wherein the wire driving means (e.g., transducer) is located at the wire tip inside the body rather than in an ex-vivo handle 12. Alternatively, one may place a mass on the wire 18 tip (mass not shown) which serves to control an acoustic reflection from the wire's end.

Figure 9:
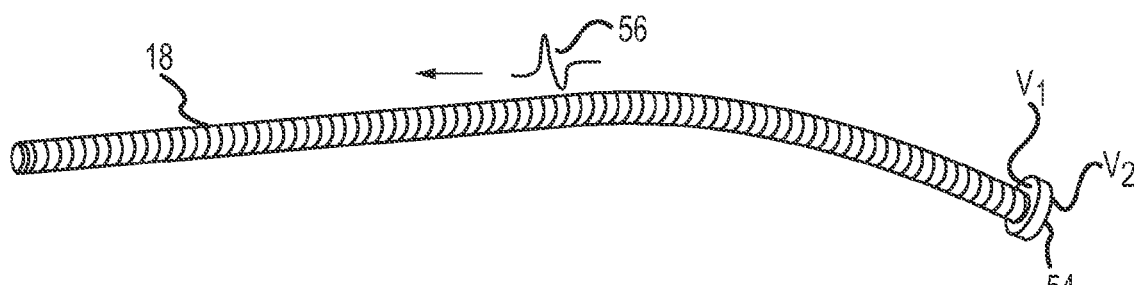
FIG. 9 is a side view of an embodiment of the present invention including a diagnostic transducer for detecting a status of the wire.

FIG. 9 shows a still further embodiment of apparatus 10 which includes a wire state assessment arrangement configured to allow assessment of the "health" or physical status of wire 18 (e.g., a reliability condition such as whether there is a crack, break or other impairment in the wire, a loading state indicative of what the state of loading may be between wire 18 and the surrounding lumen and/or sleeve 50; or other condition such as what the wire temperature may be as its velocity changes with temperature). The wire state assessment arrangement is configured to output a signal or the like indicating the result of such assessment. The principal advantage of the health status feature is that it allows a user or practitioner, or the console, to detect at an early stage the onset of a breakdown of the wire, which if undetected could result in the wire breaking while inside the patient, which sometimes occurs with prior art wires. A secondary feature theoretically allows multiple uses of a wire 18, since the integrity of the wire can be confirmed, thus offering advantages as compared to single-use or limited-use configurations known in the art. However, as understood in the art, the wire 18 would need to be suitably cleaned and sterilized, and a procedure akin to autoclaving may be required. However, as described above, the clearing wire is preferably disposable after a single use. The wire state assessment arrangement may comprise one of (1) at least an acoustics receiving transducer; (2) an acoustic "pitch/catch" transducer such as a pulse-echo transducer 54; (3) a light processing block; and (4) an electrical monitor circuit.

The acoustics receiving transducer embodiment (not shown) of the wire state assessment arrangement is configured to monitor acoustics from the clearing member 18 wherein the received acoustics are affected by a reliability condition or a loading state as described above. The monitored acoustics may include acoustics produced as a result of the operation of the acoustic driver 14, the acoustics receiving transducer and/or the clearing member itself.

The pulse-echo transducer 54 is configured for pulse-echo operation (more below) and may be a dedicated pulse-echo transducer that is different from the acoustic driver 14 or may be an integrated pulse-echo transducer incorporated within the acoustic driver 14. In operation, transducer 54 is responsive to an electrical pulsed-voltage input signal provided on input terminals V1 and V2. The input voltage pulse signal causes transducer 54 to generate an acoustic pulse 56 (shown), which travels leftward down the wire 18 and reflects from the free end thereof and travels rightward back to transducer 54 still at a detectable amplitude. Breaks, cracks, or other impairments in the wire 18, however, will alter the nature, timing and number of any reflected pulses. The transducer 54 is responsive to the reflected pulse(s) 56, which can be detected or sensed via conventional receive-circuitry. Specifically, the transducer (or associated circuitry) is configured to produce an output signal indicative of the physical condition of the wire. Such a signal will primarily comprise expected desired and undesired acoustic reflections. Transducer 54 can take many forms, including, in one embodiment, being incorporated with acoustic driver 14. Alternatively, transducer 54 may comprise a separate device or be a part of a disposable wire 18. Transducer 54 (and associated circuitry for signal processing) may comprise conventional apparatus known to those of ordinary skill in the art. According to this aspect of the present invention, defects or impending failures in wire 18 can be detected before such breakdown occurs and appropriate responses can be taken by the user or system (e.g., treatment can be discontinued and wire 18 removed from the bodily lumen and replaced).

In one embodiment, the pulse-echo waveform (i.e., the reflected diagnostic signal that is used by transducer 54) will be selected to have a much shorter wavelength than the treating wavelength used by the acoustic driver so as to attain fine axial resolution that allows acoustic monitoring of the wire health even while the wire is being excited to perform patient treatment. Transducer 54, assuming that it can receive acoustic signals from the wire (and its coupled anatomy), might alternatively be excited by the treating driver waves being reflected. Again, transducer 54 may also be the treating driving transducer or in a common stack of treating/pulse-echo transducers. The main point is that transducer 54 will preferably have an ability to resolve fine frequency components in the reflection necessary to detect wire defects.

The light processing block embodiment (not shown) of the wire state assessment arrangement is applicable where the clearing member is or comprises one or more optical fibers. In these variations, the light processing block is configured to monitor the light, if any, present on the optical fiber and determine a reliability condition or a loading state, as described above. It is known that changes in light or a complete failure to receive any (reflected) light may indicate a problem.

An electrical monitor circuit embodiment (not shown) of transducer driver section may also or alternatively be configured to monitor characteristics of the electrical power drawn by the acoustic driver and determine a reliability condition or a loading state, as described above. Changes in the current drawn by the acoustic driver 14 may be indicative of a reliability condition or a loading state.

Finally, the inventive vibrating wire may cause a pumping effect of blood or fluid along its length, particularly if it has an asymmetrical cross-section or has a surface pattern defined in or onto the wire 18 surface. A helical wire may also do this. Under such circumstances, such pumping effect may be used to deliver (or extract) one or more of cooling, contrast, cavitation, flushing or drug-delivery support.

Although numerous embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An apparatus, comprising:
   an acoustic driver configured to produce acoustic vibration in a torsional orientation;
   a flexible clearing member acoustically coupled to said driver and configured to be excited in accordance with said acoustic vibration, said clearing member comprising a wire having a longitudinal axis of torsional rotation and a treating portion of an overall axial length thereof that is configured to effect a beneficial erosive clearing action within a bodily lumen,
   wherein at least said treating portion of said wire has one or more topographical features, said wire vibrating when excited by said torsional acoustic vibration configured to effect said beneficial clearing action in the bodily lumen, wherein said at least one or more topographical features includes one of (1) an additive surface feature selected from the group comprising an electro-formed material, an electro-deposited material, an electro-plated material, an adhered material, a bonded material, and a texturing or roughening of the surface during wire formation wherein the wire formation comprises one of a drawing and an extrusion formed onto or from a surface of the wire, and (2) a subtractive feature selected from the group comprising an etched feature including a laser-etched machined feature, an electro-discharge machined feature, and a texturing or roughening of the surface during wire formation into or from a surface of the wire.

2. The apparatus of claim 1 further comprising:
   at least one of an acoustic amplifying and an acoustic matching section configured to couple said acoustic driver to said flexible clearing member.

3. The apparatus of claim 1 wherein said acoustic driver is configured, in a first mode of operation, to produce said acoustic vibration at an operating frequency within an ultrasonic frequency range, said wire rotating in a reciprocating fashion and having at least one operating amplitude no greater than a predetermined maximum operating amplitude, said acoustic driver and said flexible clearing member being configured such that rotation thereof at said operating frequency and at said at least one operating amplitude is sufficient to establish a plurality of nodes and anti-nodes within said treating portion when in the bodily lumen, whereby said clearing action is effected by cavitation of the fluid within the bodily lumen.

4. The apparatus of claim 1 wherein said acoustic driver is configured, in a second mode of operation, to produce said acoustic vibration at an operating frequency within an ultrasonic frequency range, said flexible clearing member rotating in a reciprocating fashion and having at least one operating amplitude no greater than a predetermined maximum operating amplitude, said acoustic driver and said flexible clearing member being configured such that rotation thereof at said operating frequency and at said at least one operating amplitude is below a cavitation threshold wherein said clearing action corresponds to at least one of a wire physical contact clearing and a fluidic machining clearing of said bodily lumen.

5. The apparatus of claim 3 wherein said acoustic vibration in said first mode of operation defines a continuous wave (CW) over a predefined or controlled time period configured to establish said plurality of nodes and anti-nodes within said treating portion when in the bodily lumen.

6. The apparatus of claim 4 wherein said acoustic vibration in said second mode of operation defines a continuous wave (CW) over one of a predefined and controlled time period configured to establish said plurality of nodes and anti-nodes within said treating portion when in the bodily lumen.

7. The apparatus of claim 5 wherein said continuous wave comprises a multi-waveform episode.

8. The apparatus of claim 6 wherein said continuous wave comprises a multi-waveform episode.

9. The apparatus of claim 5 wherein said acoustic driver is configured to vary said operating frequency of said acoustic vibration over said predefined or controlled time period to effect scanning of said nodes and anti-nodes axially at least along said treating portion.

10. The apparatus of claim 6 wherein said acoustic driver is configured to vary said operating frequency of said acoustic vibration over said predefined or controlled time period to effect scanning of said nodes and anti-nodes axially at least along said treating portion.

11. The apparatus of claim 1 wherein said flexible clearing member is said wire having said one or more surface features, said one or more surface features comprising at least one selected from the group comprising a temporary texturing, a permanent texturing, a temporary topography provision and a permanent topography provision.

12. The apparatus of claim 11 wherein at least one of said texturing and topography provision comprises a first material different from a second material of said wire.

13. The apparatus of claim 1 wherein said flexible clearing member comprises one of titanium material, titanium alloy material, stainless steel material, glass material, ceramic material, metal material, electrically-conductive material, optically-transmissive material and low acoustic loss material.

14. The apparatus of claim 13 wherein said optically-transmissive material comprises an optical fiber.

15. The apparatus of claim 14 wherein said optically-transmissive material comprises a plurality of optical fibers.

16. The apparatus of claim 15 where said optically-transmissive material comprises one of said plurality of optical fibers being coated and said plurality of optical fibers being impregnated.

17. The apparatus of claim 13 wherein said electrically-conductive material comprises a plurality of strands each of which are smaller than said clearing member.

18. The apparatus of claim 17 wherein electrically-conductive material comprises one of said plurality of smaller strands being wound, said plurality of smaller strands being impregnated and said plurality of smaller strands being coated.

19. The apparatus of claim 1 wherein said flexible clearing member includes one or more of a lumen, an optical core, a fiber optic element, a drug-including coating, a drug-including potting, a fiber-optic component and a hollow interior.

20. The apparatus of claim 19 wherein said flexible member includes said lumen, said lumen being configured to communicate one of a fluid pressure and a pneumatic pressure.

21. The apparatus of claim 19 wherein said flexible member includes said lumen, said lumen being configured to communicate one of a fluid flow and a pneumatic flow wherein said flow comprises at least one of a coolant liquid and a drug-delivery liquid, and wherein said flow may be in one of an inward direction and an outward direction relative to a handle of said apparatus.

22. The apparatus of claim 1 further including a mechanism for removably attaching said flexible clearing member to thereby permit removal and disposal of said clearing member after one use or removal and sanitization of the clearing member for reuse.

23. The apparatus of claim 22 wherein said mechanism comprises a pin vise.

24. The apparatus of claim 1 wherein said acoustic driver includes an auto-tuning driver circuit.

25. The apparatus of claim 24 wherein said auto-tuning circuit includes an electrical impedance matching component.

26. The apparatus of claim 1 wherein said wire is asymmetrical and, said asymmetry varies as a function of axial position along said wire.

27. The apparatus of claim 1 wherein said wire is asymmetrical at least along said treating portion.

28. The apparatus of claim 1 further including a catheter disposed outwardly of said flexible clearing member.

29. The apparatus of claim 28 wherein said catheter contains said flexible clearing member.

30. The apparatus of claim 28 wherein said catheter is configured to have a first position containing-of said treating portion to thereby enclose at least a subpart of said treating portion, said catheter being configured to have a second position axially offset and away from said first position where said at least subpart of said treating portion is exposed.

31. The apparatus of claim 28 wherein said catheter includes one or more lumens configured for at least one operation selected from the group comprising: delivering or guiding the flexible member to a treating location in the bodily lumen, delivering a desired drug to the treating location, delivering flushing or aspirated liquids to the location; removing flushing or aspirated liquids from the location; and inflating or draining a balloon portion of a balloon-based device.

32. The apparatus of claim 31 wherein one of said lumens contain said clearing member.

33. The apparatus of claim 1 further including a wire state assessment arrangement configured to produce a signal indicative of at least one of a reliability condition and a loading state of said flexible clearing member, said wire state assessment arrangement being one selected from the group comprising:
    (i) at least an acoustics receiving transducer configured to monitor acoustics from said clearing member, said acoustics being affected by said at least one of said reliability condition and said loading state, said monitored acoustics including acoustics produced by said acoustic driver, by said acoustics receiving transducer or by said clearing member;
    (ii) a pulse-echo transducer configured for pulse-echo operation, said pulse-echo transducer being at least one of a dedicated pulse-echo transducer different from said acoustic driver and an integrated pulse-echo transducer incorporated within said acoustic driver;
    (iii) a light processing block coupled to a fiber optic element comprising or within said clearing member; and
    (iv) a monitor circuit configured to monitor characteristics of the electrical power drawn by the acoustic driver.

34. The apparatus of claim 2 wherein at least one of said driver, said acoustic amplifying section and said acoustic matching section are configurable to accommodate at least one of: a) a plurality of different flexible clearing members having a corresponding plurality of different sizes, lengths and shapes to effect said clearing action, b) manufacturing tolerances in a particular wire version.

35. The apparatus of claim 1 wherein said flexible clearing member includes a free end, said apparatus further including a distal body with mass coupled to said clearing member proximate said free end to thereby provide a desired vibration characteristic.

* * * * *